United States Patent
Fischer

(10) Patent No.: US 7,522,281 B2
(45) Date of Patent: Apr. 21, 2009

(54) APPARATUS AND METHOD FOR DETECTING MOISTURE IN A PRINTING PLATE EXPOSER

(75) Inventor: Jörg-Achim Fischer, Laboe (DE)

(73) Assignee: Heidelberger Druckmaschinen AG, Heidelberg (DE)

( * ) Notice: Subject to any disclaimer, the term of this patent is extended or adjusted under 35 U.S.C. 154(b) by 287 days.

(21) Appl. No.: 11/313,127

(22) Filed: Dec. 20, 2005

(65) Prior Publication Data

US 2006/0132785 A1    Jun. 22, 2006

(30) Foreign Application Priority Data

Dec. 20, 2004   (DE) .................. 10 2004 061 189

(51) Int. Cl.
   *B41J 3/04*   (2006.01)
(52) U.S. Cl. ..................................... 356/448
(58) Field of Classification Search ................. 356/445, 356/446; 347/102; *B41M 7/00*
   See application file for complete search history.

(56) References Cited

U.S. PATENT DOCUMENTS

| | | | | |
|---|---|---|---|---|
| 4,565,450 A | * | 1/1986 | Wirz et al. ................. | 356/402 |
| 5,162,865 A | * | 11/1992 | Kipphan et al. ............ | 356/138 |
| 5,645,738 A | | 7/1997 | Cecil | |
| 6,457,801 B1 | | 10/2002 | Fish et al. | |
| 6,562,413 B1 | * | 5/2003 | Morgavi .................... | 427/466 |
| 6,854,841 B1 | * | 2/2005 | Unter ....................... | 347/102 |
| 2003/0183099 A1 | * | 10/2003 | De Vroome ................ | 101/148 |
| 2004/0119772 A1 | * | 6/2004 | Hoshino et al. ............. | 347/19 |

FOREIGN PATENT DOCUMENTS

| | | |
|---|---|---|
| DE | 2 214 721 | 6/1973 |
| DE | 32 20 282 A1 | 12/1983 |
| DE | 44 36 582 A1 | 4/1996 |
| DE | 103 08 436 B3 | 5/2004 |
| EP | 0 000 689 | 6/1978 |
| EP | 0 177 921 | 10/1985 |
| EP | 0 202 803 A2 * | 11/1986 |
| GB | 1 393 856 | 5/1975 |
| JP | 62-207650 | * 9/1987 |

* cited by examiner

*Primary Examiner*—L. G Lauchman
*Assistant Examiner*—Rebecca C Slomski
(74) *Attorney, Agent, or Firm*—Laurence A. Greenberg; Werner H. Stemer; Ralph E. Locher

(57) ABSTRACT

In temperature-controlled printing plate exposers, it is possible for condensation of dampening solution or moisture to occur in a region of printing plates or laser apparatus. In this way, imaging of printing plates can be impaired and/or the laser apparatus can suffer damage resulting from corrosion. An apparatus detects the quantity of dampening solution on a measuring spot in an exposer for printing forms. The intention is for the ingress of condensation within a printing plate exposer to be detected more accurately. A measuring beam having a first intensity is reflected from the measuring spot and a measured signal is generated at a photoelectric conductor. Following evaporation of the dampening layer on the measuring spot, a reference signal is generated at a photoelectric converter by reflected radiation from the measuring spot. By comparing a measured signal and a reference signal, the dampening solution or moisture can be detected.

23 Claims, 4 Drawing Sheets

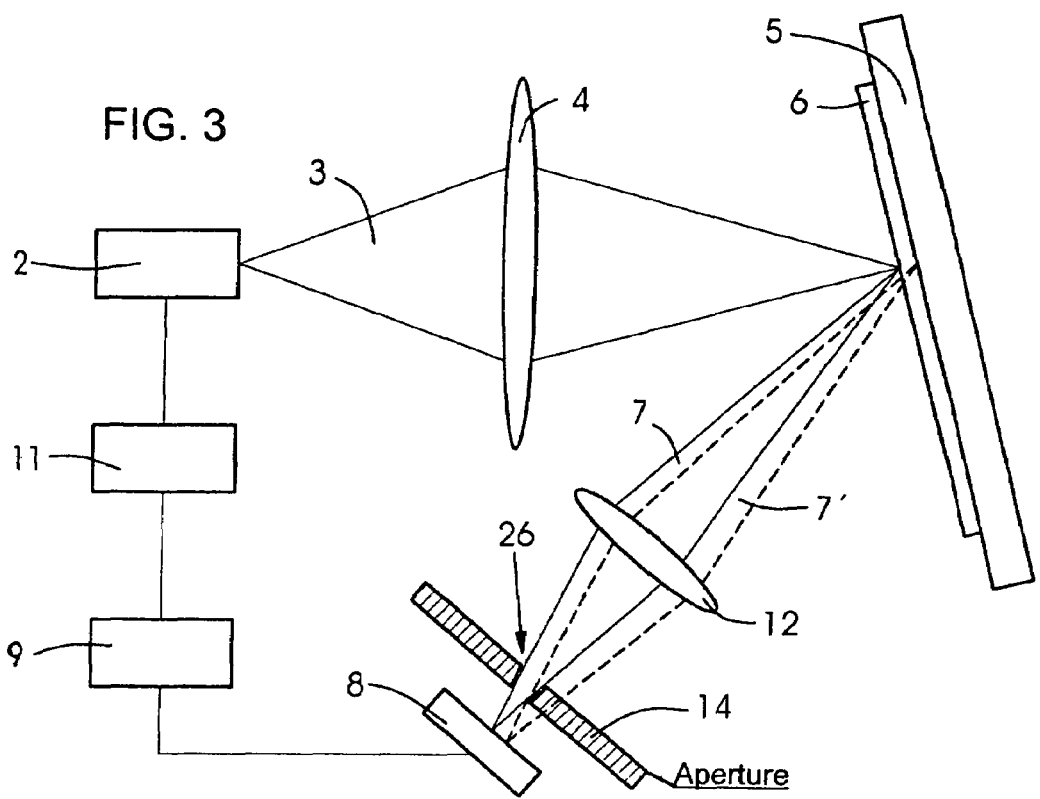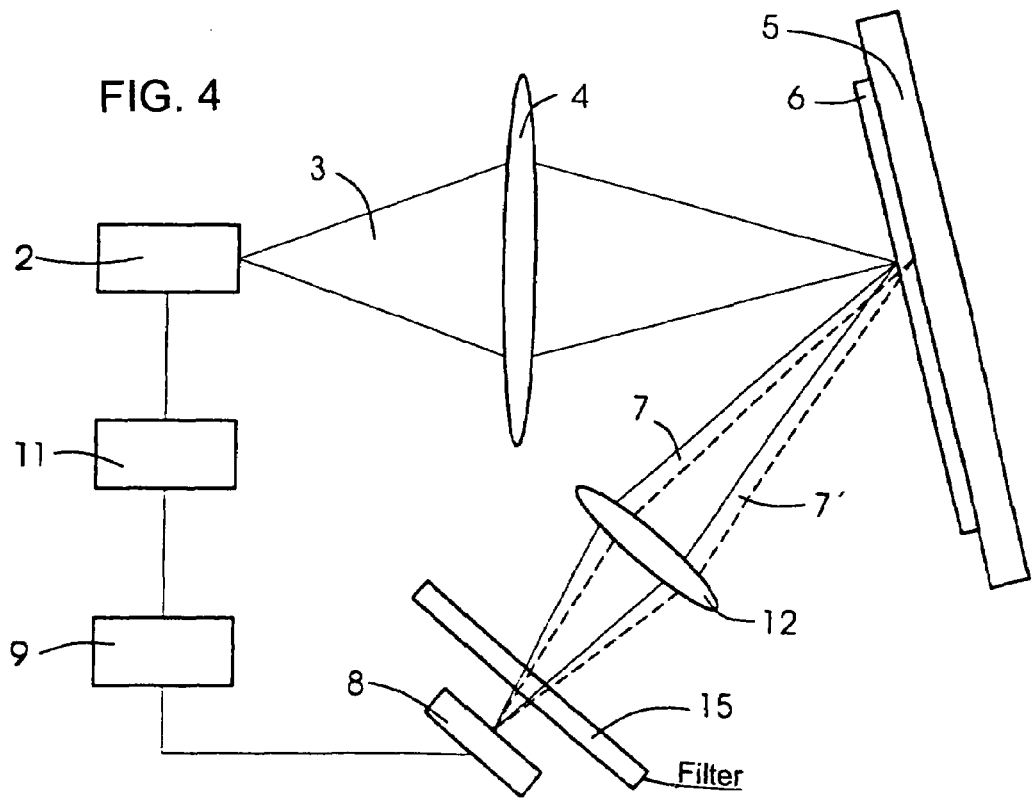

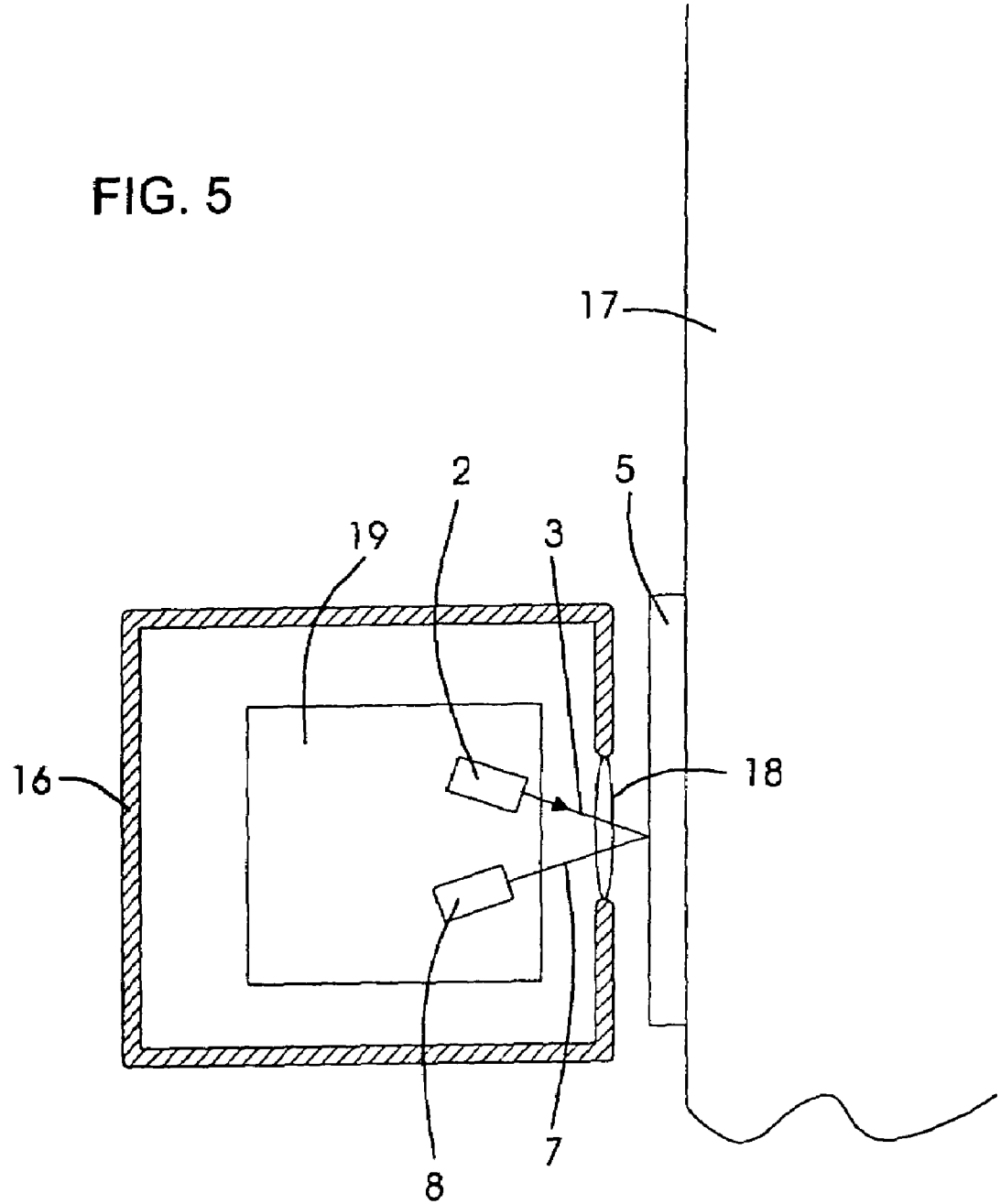

APPARATUS AND METHOD FOR DETECTING MOISTURE IN A PRINTING PLATE EXPOSER

BACKGROUND OF THE INVENTION

Field of the Invention

The present invention relates to an apparatus and a method for detecting a quantity of moisture on a measuring spot in an exposer for printing forms.

In reproduction technology, printing forms which contain all the elements to be printed such as texts, graphics and images are produced. For color printing, a separate printing form is produced for each printing ink. For four-color printing, these are the printing inks cyan, magenta, yellow and black (CMYK). The printing forms separated in accordance with printing inks are also referred to as color separations.

The information to be printed is first transferred from printing originals to the printing form. Depending on the printing form there are different methods for transferring the printing original to the printing form. It is possible for films first to be exposed in an exposer, with which films printing plates for the printing of large editions are produced. For this purpose, the printing original is screened and subsequently exposed onto the film with an exposer. Alternatively, the printing originals can also be exposed directly onto printing plates in specific imaging devices such as printing plate exposers. The exposure of the printing plates can also be carried out directly within a printing press.

The data for a printing original is nowadays generally available in electronic form and is converted into the CMYK color separations in a raster image processor (RIP) or in advance.

During the exposure of a printing plate of a color separation, individual halftone dots are assembled from smaller exposure points. The color separation itself then is formed of the set of exposure points. The exposure points on the printing plate are generally exposed onto the plate by a laser. They are approximately an order of magnitude smaller than the halftone dots. A typical resolution of the exposure points is, for example, 1000 exposure points per centimeter, that is to say an exposure point has the dimension 10 µm×10 µm. In this case, the printing original can be exposed onto the surface of the printing plate by one or more lasers or by what is known as a laser rake. In this case, the laser or lasers scan the entire surface of the printing plate. For this purpose, the laser can be moved relative to the printing plate, the printing plate can be moved relative to the laser or the two can be moved relative to each other.

In what are known as in-drum or internal drum exposers, the printing plate is clamped on within a cylinder and the laser beam is deflected along the axes of the printing plate cylinder by optical elements and deflected onto the surface of the printing plate. For this purpose, for example, a rotating prism can be provided axially within the printing plate cylinder. The rotating prism is set rotating in order to deflect the laser beam and in this way scans the surface of the printing plate in what is known as a fast scan direction. In addition, the rotating prism experiences a forward displacement, by which the surface of the printing plate is scanned in a slow scan direction. Instead of rotating prisms, mirrors can also be used. In what are known as ex-drum or external drum exposers, the printing plate is clamped onto the surface of the drum on the outside. The laser beam for imaging the printing plate can be deflected onto the surface of the printing plate directly or via optical elements. The drum is set rotating, while the exposer unit, containing the exposure lasers and/or any optical elements, is moved along a forward displacement direction. The direction of rotation of the printing plate then corresponds to the negative fast scan direction, while the forward displacement direction of the exposer unit describes the slow scan direction of the imaging of the printing plate.

During the exposure of the printing originals onto a printing form, care must be taken that the position of the exposed area in relation to the edges of the printing form or in relation to what are known as punched screen portions of the printing form is the same for all the color separations of a printed sheet. Otherwise, it is possible for color separations not to be printed congruently over one another in the press. Corresponding deviations can be seen clearly in the printed image.

Printing plates are generally composed of a carrier material, for example aluminum with a thickness in the range from 0.1 mm to 0.3 mm. They change their dimensions, for example as a result of temperature-induced longitudinal expansions, by about 24 um per ° C. and per meter edge length. If non-identical temperature conditions prevail during the setting up of different color separations for printed sheet, then the printing plates will be distorted correspondingly differently and, during the subsequent printing process, the printed color separations will not be printed identically above one another. The consequence is a detectable deficiency in the quality in the printed image. Different ambient influences can occur, for example, when individual color separations are imaged in different plate exposers or with an offset in time. This can be the case in particular when the printing plate is damaged during the printing process and has to be imaged again. In order to produce ambient conditions which are always the same, provision can therefore be made for the printing plate exposers all to be set up in an air-conditioned room. This solution is relatively expensive. Other solutions consist in the drums of the printing plate exposers having their temperature controlled. There are various possibilities for this, for example, German patent DE 103 08 436 (corresponding to U.S. patent publication 2004/0168602) discloses leading a temperature-controlled liquid through an inner tube in an ex-drum exposer. The temperature-controlled liquid then ensures a uniform temperature of the printing plate cylinder. Corresponding temperature control systems for other types of exposer are conceivable. The advantage of this solution is that, economically, only the printing plate exposers have to be set up appropriately. Air-conditioning the room in which the printing plate exposers are located is not necessary. In this way, it is advantageously possible to ensure that the surfaces of different printing plate cylinders are at the same temperature in each case.

In this printing plate cylinder temperature control device, effects which occur as a function of further environmental variables are problematic. Depending on the external air pressure, temperature or atmospheric humidity, condensation of moisture occurs on the surface of the drum or the printing plate. In this way, the imaging of the printing form is impaired considerably. If the printing plate exposer is in a warm environment, for example, which can have an increased humidity, it is possible for condensation of water to occur on the printing plate cylinder, which is then cooled. As a result of this formation of water on the surface, in addition to impairment of the imaging process, it is additionally possible for other problems such as corrosion, short circuits and so on to occur. This is true in particular of the regions of the printing plate exposer in which the laser devices are kept ready. It is also possible to provide for the laser devices to have their temperature controlled. Should water condense in these regions, then damage to the laser devices can occur.

In order to image a printing form, it is necessary to detect moisture, for example on the drum or the printing plate itself, in good time. For this purpose, published nonprosecuted German patent application DE 32 20 282 A1, corresponding to U.S. Pat. No. 4,565,450, discloses irradiating a measuring spot with radiation by a radiation device and detecting and evaluating the reflected radiation from the measuring spot with the aid of a photoelectric converter. In addition, an evaluation circuit is provided for this purpose. In this device, a first measured signal is generated in which the measuring spot is irradiated in a dry state and the dry value is stored. During a printing process, in which the printing plate is then dampened, a corresponding second measured value is generated, which represents a measure of the quantity of moisture on the printing plate. The actual quantity of moisture on the printing plate can be determined from a comparison of the reference signal with a measured signal. The device and the method presented here are applied within a press for offset printing, where the surface of the printing plate has moisture applied to it for the printing process. The reference signal is generated during the printing pauses here, irrespective of the environmental variables. In this method, dampening solution itself is intended to be found on the printing plate and its quantity is to be determined. The transition between a dry plate and condensed dampening solution or moisture on the plate cannot be determined accurately here. The reference value is obtained at an arbitrary point in time. In the method described, it is not possible to rule out that there is already condensed moisture on the printing plate.

SUMMARY OF THE INVENTION

It is accordingly an object of the invention to provide an apparatus and a method for detecting moisture in a printing plate exposer which overcome the above-mentioned disadvantages of the prior art devices and methods of this general type, with which the ingress of condensation within a printing plate exposer can be detected more accurately. In particular, this method and this apparatus are intended to function independently of any drifting of measuring devices.

With the foregoing and other objects in view there is provided, in accordance with the invention, an apparatus for detecting a quantity of moisture on a measuring spot in an exposer for printing forms. The apparatus contains a radiation source for emitting radiation and at least one level controller for driving at least the radiation source at least for an emission of a measuring beam having a first intensity to generate a measuring signal determined from the radiation reflected from the measuring spot and/or a power pulse having a second intensity, being higher than the first intensity, for a substantially complete evaporation of the moisture on the measuring spot. A photoelectric converter is provided for detecting the radiation reflected or scattered by the measuring spot. The radiation emitted by the radiation source has a wavelength lying within an absorption wavelength range of the quantity of moisture on the measuring spot. An evaluation device compares the measuring signal dependent on the radiation reflected from the measuring spot with an electric reference signal determined from the radiation reflected from a dry measuring spot.

In terms of the apparatus, the object of the invention is achieved by at least one level controller for driving at least a first radiation source. In this case, the radiation source is to be driven in such a way that it emits a measuring beam having a first intensity, which is in turn reflected from a measuring spot. The radiation reflected or scattered in this way from the measuring spot strikes a photoelectric converter which is provided, which generates a corresponding measured signal. This measuring beam can either be a single laser pulse or a substantially continuous laser signal.

Furthermore, the level controller is advantageously intended to be provided such that the laser produces a power pulse having a second, higher intensity for the purpose of substantially complete evaporation of moisture on the measuring spot. By use of this apparatus, it is advantageously possible to achieve the object of the invention in the direction of the method in that at least one measuring beam having a first intensity is emitted by the first radiation source and generates a measured signal on the photoelectric converter, in a further method step, the moisture on the surface of the measuring spot is evaporated, and in that an electric reference signal is generated by the reflection of a measuring beam of the first intensity at the surface of the dry measuring spot substantially following the evaporation of the moisture. In particular, it is also possible for a reference signal to be generated first, and for the moisture to be evaporated in a manner other than by using a laser beam.

As a result of the evaporation of the moisture on the surface of the measuring spot, a guaranteed dry measuring spot can be achieved. A corresponding measuring beam from the first radiation source is then reflected from this dry area. The reflected light or at least parts thereof then generate a corresponding signal on the photoelectric converter. This signal can then be used as a reference signal. Before the generation of the reference signal, that is to say before the drying of the measuring spot, a corresponding measuring beam having the first intensity can be reflected from the surface of the measuring spot. In this way, a signal is also generated on the photoelectric conductor which, in the following text, is designated a measured signal.

This signal can alternatively also be generated following the generation of the reference signal. The chronological interval must then be chosen to be sufficiently large, so that, given corresponding ambient influences, moisture can be deposited on the measuring spot again.

The reference signal and the measured signal can be compared by an evaluation device and, depending on the difference, conclusions can be drawn about the moisture on the measuring spot. In particular, in terms of the method, provision is made for a measured signal to be generated first and for the surface of the measuring spot then to be dried, in particular by the moisture being evaporated. This can be carried out, for example, by heating up the measuring spot. By use of a subsequent measuring pulse, a reference signal is then generated. In this case, the measuring spot can be located at any desired location of the plate exposer. It should at least also be temperature-controlled and at least have no higher temperature than the remaining regions of the plate exposer. If moisture is deposited on the surface of the exposer drum or in another region of the exposer, for example in the surroundings of the laser electronics, then it will also be deposited on the surface of the measuring spot. By generating a current reference signal, the moisture can then be detected irrespective of any drift of the measuring apparatus.

For this purpose, the measuring spot can be provided, for example, in the immediate vicinity of temperature-controlled devices of the printing plate exposer. This can be, for example, the drum or else regions of the laser devices. A region which has the lowest temperature should preferably be chosen.

In terms of the method, provision is also made that, in order to evaporate the moisture, a power pulse having a second intensity, which is higher than the first intensity, is emitted. In this way, it is possible in practice in particular to free from moisture the area of the measuring spot from which the measuring beam is reflected. For this purpose, the second intensity is chosen such that the moisture on the measuring spot can evaporate; the length of the pulse should have a sufficient duration in order to evaporate possible moisture completely.

In terms of the method, provision can be made that, in a further embodiment, the power pulse is emitted by a second radiation source. For this purpose, in particular a radiation source having radiation of a higher frequency can be used. The evaporation of the moisture on the measuring spot surface can be carried out more quickly as a result. In terms of the apparatus, a second radiation source is advantageously provided for this purpose, which is driven by a level controller in order to emit the power pulse. The level controller can in particular be the same level controller that is already driving the first radiation source.

Advantageously, provision is also made for the radiation from the second radiation source to lie within a wavelength range which is covered by the wavelength range in which the surface of the measuring spot absorbs radiation. For this purpose, for example, a powerful laser diode can be provided which emits light in a wavelength range around 830 nm. A laser diode for producing a measuring beam can then emit radiation in a region around 1500 nm, for example. For the measuring beam it can be a lower-energy embodiment. In the region around 1500 nm, water absorbs particularly well.

The ratio between the wavelength of the second radiation source and the surface of the measuring spot is to be interpreted in particular, according to the invention, such that the surface coating of the measuring spot can also be matched to the wavelength in such a way that it absorbs this wavelength particularly well.

In an alternative embodiment, provision is made for the surface of the measuring spot to contain at least one absorber layer for a wavelength range which includes the wavelength of the first and/or second radiation source. It can be, for example, a black anodized metal area. In this way, it is advantageously possible that, for example, only the first radiation source is needed, with a measuring beam of a first intensity and a power pulse of a second intensity. The radiation can then lie in the wavelength vicinity of 1500 nm and will then be absorbed both by a possible moisture layer and also by the surface of the measuring spot.

An increase in the intensity of the first radiation source is then sufficient to evaporate the moisture layer, since the radiation is not only absorbed by the water but also by the measuring spot, and the moisture is also heated in a corresponding way thereby. Alternatively, the surface can also be matched appropriately to the wavelength of a second radiation source. It is then also possible for the moisture layer to be evaporated more quickly.

In a further refinement of the apparatus, provision is made for the surface of the measuring spot to be a thermally conductive layer. In particular, this layer is to be configured in such a way that it absorbs in particular radiation in the wavelength range of the power pulse. The layer heated up in this way distributes the heat quickly and uniformly on the surface of the measuring spot and evaporates a large area of condensed moisture directly. As a result, a lower accuracy is advantageously required in the local superimposition of the power pulse from the second radiation source on the measuring beam from the first radiation source. A further advantage of the thermally conductive layer is that moisture is deposited again rapidly. As a result, the interval between two measurements can be kept shorter and dampening solution can be detected more accurately and more quickly. In particular, provision is made for the measuring spot to be a metallic surface.

In a further embodiment of the apparatus, provision is made for at least one active cooling element to be provided for cooling the measuring spot. In this way, it is advantageously possible to achieve the situation in which the measuring spot has a temperature which is lower than the temperature of the printing plate stretched on the drum or of other regions of the printing plate exposer. Moisture will then be deposited on the measuring spot first and can be detected here early, even before the condensation of moisture on the printing plate or in the region of the lasers.

In terms of the method, provision is further made for a difference signal to be formed from the measured signal and the reference signal. This difference signal can advantageously be compared with stored values. From these values, it is then possible to draw conclusions about a specific state of the measuring spot. The stored values can be stored, for example, in the form of a look-up table and correspond to specific thicknesses of moisture on the measuring spot. For this purpose, these values can have been produced under laboratory conditions.

In a further refinement, according to the method provision is made for condensed moisture on the measuring spot to be detected beginning from a threshold value of the difference signal. This threshold value can be stored in a memory for this purpose. Should this threshold value be exceeded, an appropriate alarm signal can be displayed to the user of the printing plate exposer and/or exposure can be prevented; it is of course also possible for countermeasures, such as the drying of the air in the interior of the printing plate exposer, to be carried out automatically.

In a particular embodiment, provision is advantageously made that, according to the method, measured signals and reference signals are generated as a function of the intensity of the reflected radiation. For this purpose, the photoelectric converter is positioned in the beam path in such a way that the reflected light can be measured directly. A change in the intensity of the reflected light then points to moisture on the measuring spot.

In an alternative procedure, provision is made for measured signals and reference signals to be generated as a function of the intensity of the scattered light from the radiation incident on the measuring spot. For this purpose, provision is in particular made for the photoelectric converter to be positioned in a region which is not in the beam path of the reflected measuring beam or power beam. Here, advantageously, no high requirement is placed on the positioning of the photoelectric converter.

In another alternative embodiment, provision is made, according to the method, for measuring signals and reference signals to be generated as a function of the plane of polarization of the radiation reflected from the measuring spot. Use is made for this purpose of the fact that the measuring radiation used is polarized laser light. If there is water on the surface of the measuring spot, then the plane of polarization of the laser light is rotated as a function of the thickness of the moisture layer. A polarization filter is positioned in front of the photoelectric converter, which results in that the rotation of the plane of polarization is detected on the basis of a lower intensity of the radiation incident on the photoelectric converter.

In a further advantageous alternative embodiment, provision is made, according to the method, for measuring signals and reference signals to be generated as a function of the reflection angle of the radiation reflected from the measuring spot. For this purpose, use is made of the fact that the water which is deposited on the surface of the measuring spot has a refractive index differing from that of the surface of the measuring spot itself. Depending on the layer thickness, the reflection angle changes. Here, the photoelectric converter used can in particular be a matrix. In this way, a displacement of the point at which the reflected laser beam strikes the matrix can be detected and assigned to a specific, at least changed, layer thickness. It is also possible for an aperture stop to be placed in front of a photoelectric converter. A change in the reflection angle then leads to less reflected laser light being able to pass through the opening of the aperture stop onto the photoelectric converter. A change in the reflection angle then results in a lower measured signal.

In a further advantageous embodiment, whose advantages have already been described, provision is made for the measuring spot to be cooled actively.

In an advantageous further development of the invention, provision is made for the amount of energy of the power pulse to be varied in successive measurements.

In this way, the amount of energy which is needed to evaporate a possible dampening layer on the surface of the measuring spot completely can be reached iteratively.

In an advantageous further development, provision is made for the amount of energy to be varied in successive measurements in that, starting from a minimum value, it is increased until no changes in successive reference signals can be detected.

In this way, it is beneficially possible for this reference signal, which no longer changes from one measurement to a following measurement, to be identified unambiguously as a reference signal which is assigned to a surface of the measuring spot which no longer has a layer of moisture applied to it.

In a possible further development, provision is advantageously made for the amount of energy to be varied by changing the second intensity of the power pulse. In this way, the amount of energy can be varied simply.

In an alternative embodiment, provision is made for the amount of energy to be varied by changing the pulse length of the power pulse. This constitutes a further advantageously simple way of varying the amount of energy of the power pulse.

In a particularly advantageous development of the invention, provision is made for no measuring beam to be emitted and for moisture to be detected by using the amount of energy of the power pulse which is needed in order that no changes occur in the reference signal.

In this way, the measurement which is needed in order to detect the moisture can advantageously be simplified. Only one beam from the radiation source is still needed for each measurement. These measurements can then be carried out successively, the amount of energy of this beam being varied. If the amounts of energy are increased in each case then, in a further advantageous embodiment, by using the amount of energy which is needed in order that no changes occur in the measured reference signal, conclusions can be drawn about the thickness of the moisture layer. In particular, it is also simply possible to draw conclusions about the presence of a moisture layer as such.

Of course, after two successive measurements with changed amounts of energy of the power pulse, it is also simply possible to draw conclusions about a dampening layer. If, in spite of varied amounts of energy, no change occurs in the measured reference signals, then it is possible to draw conclusions directly about the presence of a dampening layer. In particular, it is possible to draw conclusions about the thickness of the dampening layer by an iterative method if the amount of energy is varied to such an extent that, given a lasting increase in the amount of energy, changes in the reference signal could no longer be detected only in a third or subsequent measurement step.

In particular, provision is made that, for all possible combinations for the detection of moisture on the measuring spot, a comparison with stored look-up tables is possible. In this way, the layer thickness of the amount of moisture on the measuring spot can be detected directly.

The method described and the corresponding apparatus for its implementation can be applied in all types of printing form exposers.

Other features which are considered as characteristic for the invention are set forth in the appended claims.

Although the invention is illustrated and described herein as embodied in an apparatus and a method for detecting moisture in a printing plate exposer, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 3 is an illustration showing an alternative apparatus for detecting the moisture layer via reflected radiation;

FIG. 4 is an illustration showing a further alternative apparatus for detecting the moisture layer via reflected radiation;

FIG. 5 is an illustration showing a possible installation of the apparatus from the preceding figures;

DESCRIPTION OF THE PREFERRED EMBODIMENTS

Figure 1:
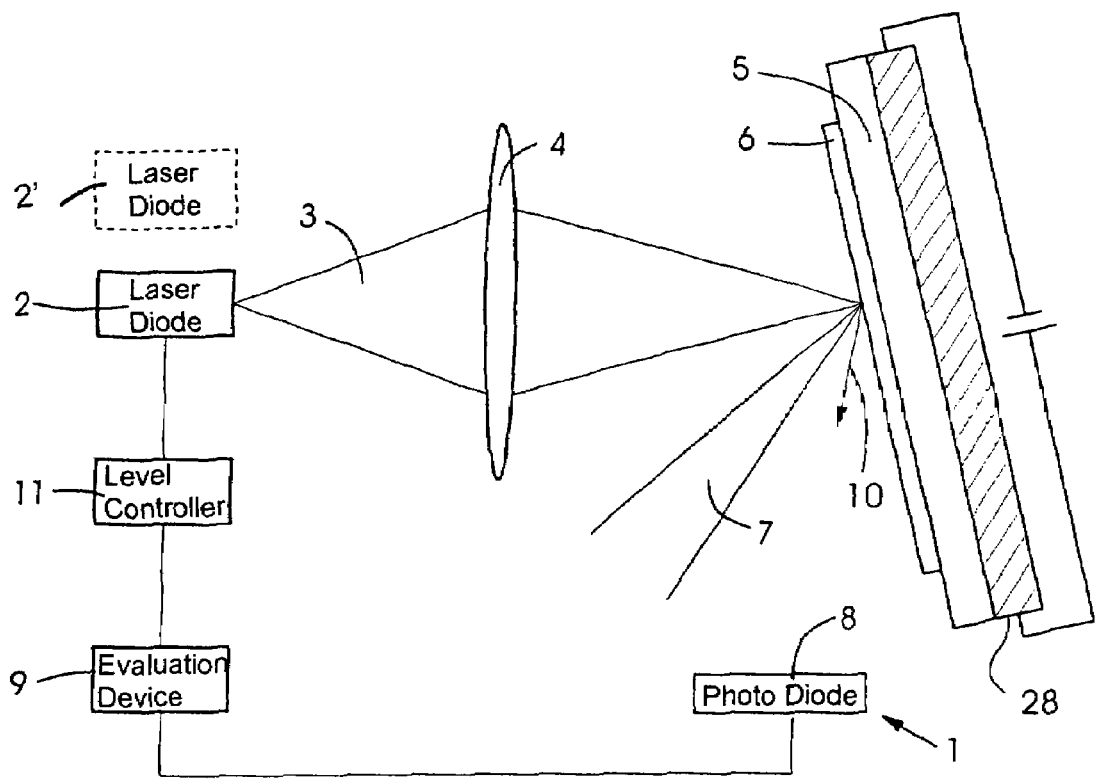
FIG. 1 is an illustration showing an apparatus for detecting a moisture layer via scattered light according to the invention.

Referring now to the figures of the drawing in detail and first, particularly, to FIG. 1 thereof, there is shown, in schematic form, an apparatus 1 for detecting a moisture layer 6 on a measuring spot 5. In this case, the measuring spot 5 is a metal surface, for example. This should be located at the coldest location possible of a printing plate exposer. For example, the measuring area 5 can be provided in the region of the drum of the printing plate exposer.

A laser diode 2 is driven via a level controller 11 for the purpose of emitting laser beams 3. Depending on the driving by the level controller 11, laser beams 3 having different intensities $I_M$ and $I_L$ are emitted. In this case, $I_M$ is the intensity of a measuring beam 20 and $I_L$ is the intensity of a power pulse 22. The intensity IL of the power pulse 22 exceeds the intensity $I_M$ of the measuring beam 20.

Irrespective of whether the laser beam 3 is emitted as a measuring beam 20 or a power pulse 22, the laser beam 3 is first focused onto a surface of the measuring spot 5 by a focusing lens 4. The laser beam 3 is reflected from the measuring spot here as a reflected laser beam 7. In addition to the reflected laser beam 7, the formation of scattered light 10 occurs. The intensity of scattered light 10 depends on the moisture layer 6 which may possibly be located on the measuring spot 5. This dependence is brought about, for example, by irregularities in the measuring spot 5, which are covered by the liquid layer 6. A smooth surface is produced in this way, which results in that less scattered light 10 is produced. Part of the scattered light 10 falls onto a photodiode 8. The photodiode 8 is located outside the beam path of the reflected laser beam 7. As a result of the incident scattered light 10, the photodiode 8 generates an electronic signal. This signal is passed on to an evaluation device 9. In the evaluation device 9, electric signals from the photodiode 8 which have their origin in measuring beams 20 at different times are compared with one another. There will be more on this later.

Figure 2:
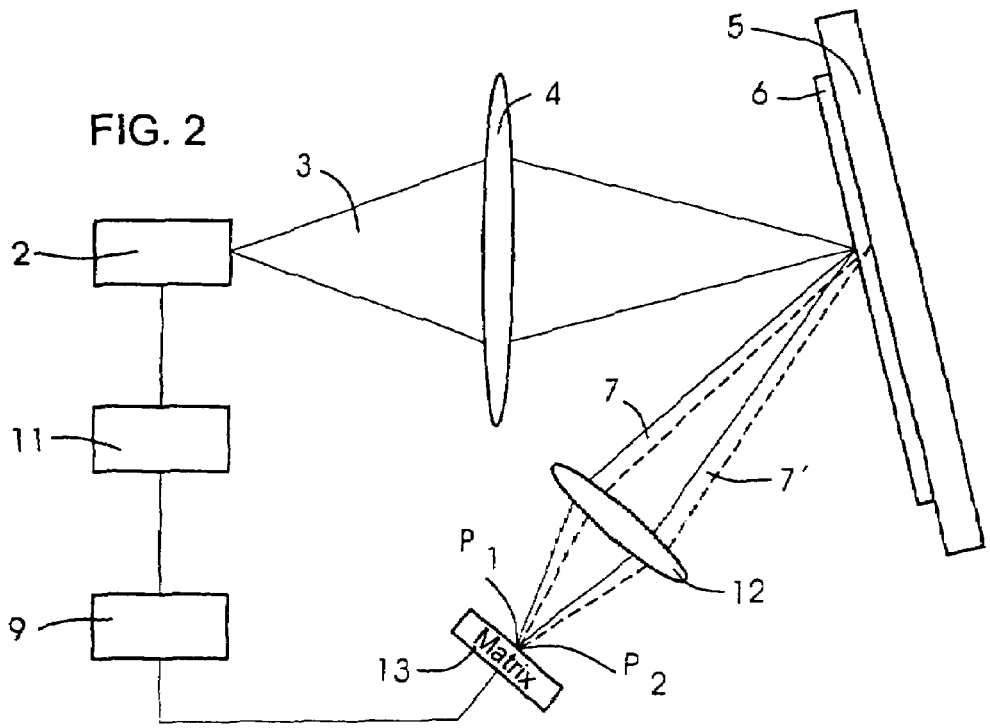
FIG. 2 is an illustration showing an apparatus for detecting the moisture layer via reflected radiation.

FIG. 2 shows an alternative apparatus 1 for detecting the moisture layer 6 on the measuring spot 5, the reflected laser beam 7 being used here. Here, the same reference numbers designate the same elements as in FIG. 1.

As in FIG. 1, the laser beam 3 is emitted by the laser diode 2, focused onto the measuring spot 5 by the focusing lens 4, in order then to be reflected. The reflected beam 7 is deflected differently, depending on the moisture layer 6 on the measuring spot 5. The origin of this resides in the refractive index N of the moisture layer 6, which is different from one. The reflected laser beam 7 of a surface of the measuring spot 5 which is not covered by the moisture layer 6 is displaced by the moisture layer 6 toward a beam path of a reflected laser beam 7'. In the setup presented here, provision is made for the reflected radiation 7, 7' to be focused onto a matrix 13 by a further focusing lens 12. The matrix 13 can be, for example, a CCD matrix. Depending on the thickness of the moisture layer 6, the reflected laser beam 7, 7' is focused at a point P1 or P2 of the matrix 13. The electronic signals generated in this way can then be passed on to the evaluation device 9.

In the evaluation device 9, the signals from the reflected laser beams 7, 7' can be compared with each other. In the case illustrated here, the respective signals differ in the positions of the CCD sensors which detect the reflected laser radiation 7 or 7'. Depending on the location P1 or P2 at which the reflected laser radiation 7, 7' is detected, it is then possible to decide about the presence of the moisture layer 6 on the measuring spot 5. In particular, the signals obtained in this way can be compared with a look-up table and it is possible to decide about the layer thickness of the moisture layer 6.

An alternative embodiment of the apparatus for detecting moisture solution 6 on the measuring spot 5 is illustrated in FIG. 3, use again being made here of the reflected radiation 7, 7' in order to decide about the moisture layer 6 that is present on the measuring spot 5. Identical elements are again designated by the same reference numbers.

Depending on whether the moisture layer 6 is present on the measuring spot 5 and depending on its layer thickness, the reflected radiation 7 or 7' will have a different beam path. The reflected radiation 7, 7' is again focused by a focusing lens 12 in such a way that it is focused on a photodiode 8. Here, an aperture stop 14 is positioned in front of the photodiode 8. The aperture stop 14 is dimensioned such that the reflected radiation 7 which is reflected from the measuring spot 5 when there is no moisture layer 6 present on the latter can just pass through an opening 26 without proportions of the reflected radiation 7 being shielded off.

If there is a moisture layer 6 on the measuring spot 5, the reflected radiation 7' will follow a different beam path than the reflected radiation 7. The reflected radiation 7' is then also focused on to the photodiode 8 by the focusing lens 12. In this case, however, it is screened off by part of the aperture stop 14. Only part of the reflected radiation 7' falls onto the photodiode 8. In this way, a smaller electric signal is generated by the photodiode 8 than as a result of the reflected radiation 7.

At specific times T1, the moisture layer 6 on the measuring spot 5 is evaporated in a defined way. In the case outlined here, this can be done, for example, via the power pulse 22. Following the evaporation, a reference signal 24 is generated on the photodiode 8. For this purpose, the laser beam 3 is focused onto the measuring spot 5 as a measuring beam 20. The measuring spot 5 now definitely has no moisture layer 6, and the reflected radiation 7 falls onto the photodiode 8. The electric signal generated here then corresponds to the reference signals 24. The reference signal 24 is passed on to the evaluation device 9. In the evaluation device 9, a measured signal 23 can then be compared with the reference signal 24. The measured signal 23 can, for example, be generated before the evaporation of the possible moisture layer 6. For this purpose, the laser beam 3 is deflected onto the surface of the measuring spot 5 with the first intensity $T_M$ as a measuring beam 20. Depending on whether there is a moisture layer 6 or no moisture layer 6 on the surface of the measuring spot 5, a reflected laser beam 7 or 7' is generated. As described, different electric measured signals 23 are generated at the photodiode 8 as a result. In the evaluation device 9, the reference signals 24 are then subtracted from the measured signals 23. In this way, a difference signal 25 is formed, which depends on the thickness of a possible moisture layer 6. If, for example, there is no moisture layer 6 on the measuring spot 5, then the difference signal 25 is equal to zero. Depending on the level of the difference signal 25, the plate exposer can be switched off or it is possible for a signal to be generated which provides information about the presence of a moisture layer 6 on the measuring spot 5. An operator of the printing plate exposer can then decide about the further operation of the printing plate exposer.

FIG. 4 shows a further alternative structure for detecting the moisture layer 6 on a measuring spot 5. Identical reference numbers again signify identical elements here.

As distinct from FIG. 3, here the reflected laser beam 7 or 7', after being focused by the focusing lens 12, is deflected through a polarizing filter 15 placed in front of the photodiode 8. Depending on the plane of polarization of the reflected laser beam 7, 7', different intensities of laser radiation then fall onto the photodiode 8. In this way, different measured signals 23 are again generated by the photodiode 8. The mode of action of this structure is that the laser light 3 emitted by the laser diode 2 is polarized in a specific plane. Depending on the thickness of a possible moisture layer 6 on the measuring spot 5, the plane of polarization of the reflected laser beam 7 or 7' is rotated. By use of the polarizing filter 15, corresponding proportions of the reflected laser radiation 7, 7' are then filtered out. By comparisons between the measured signals 23 generated in this way and reference signals 24, difference signals 25 can then again be generated, which can give information about the presence of a moisture layer 6 or its thickness.

One possible practical embodiment of an apparatus according to the invention for detecting the moisture layer 6 on a measuring spot 5 is illustrated in the manner of a sketch in FIG. 5.

In the case illustrated here, there is no moisture layer 6 on the measuring spot 5; the laser diode 2 is located on a printed circuit board 19, as is the photodiode 8. Also located on the printed circuit board 19 are the other electronic components, not illustrated here, such as the evaluation device 9 and the level controller 11. The printed circuit board 19 with the photodiode 8 and the laser diode 2 are enclosed by a housing 16. The housing 16 has a focusing lens 18 which lies both in the beam path of the laser beam 3 emitted by the laser diode 2 and also of the laser beam 7 reflected from the measuring spot 5. The distances of the photodiode 8 and the laser diode 2 and of the measuring spot 5 from the focusing lens 18 are chosen appropriately in this case such that the laser light, that is to say the laser beam 3 and also the laser beam 7, are in each case focused on the measuring spot 5 and the photodiode 8, respectively. Here, the measuring spot 5 is located on a component of a plate exposer 17; the entire evaluation device is located within the housing 16, on the printed circuit board 19.

Figure 6:
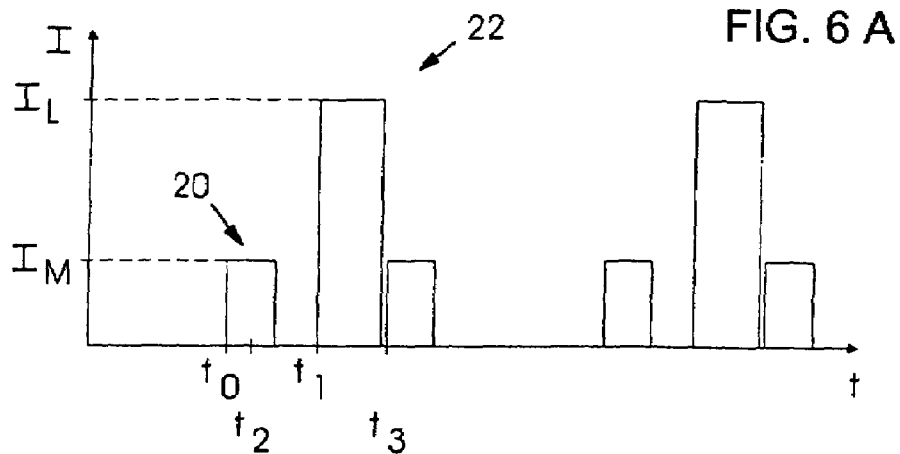
FIG. 6A is a graph showing a signal sequence for detecting the moisture layer on a measuring spot.
FIG. 6B is a graph showing a further possible signal sequence for detecting the moisture layer on a measuring spot.
Figure 6:
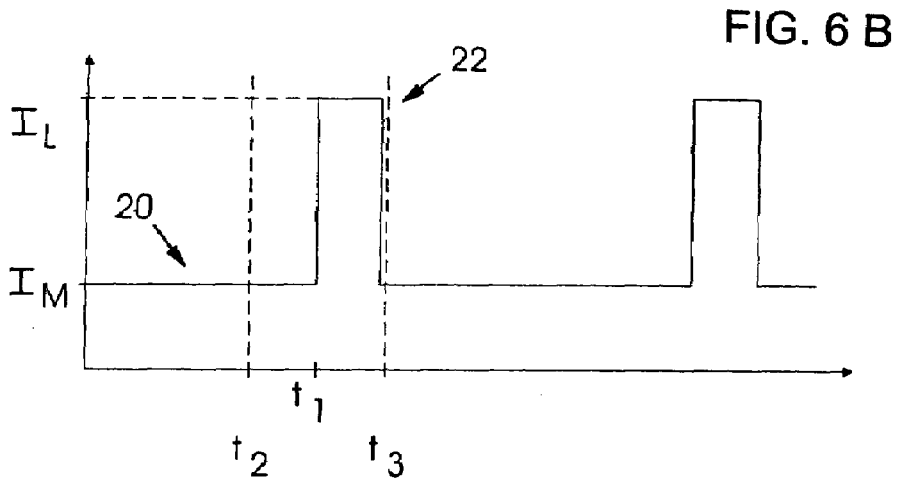

In FIGS. 6A and 6B, possible signal sequences for the laser beam 3 are illustrated over time. In FIG. 6A it is shown that the laser beam 3 is broken down into individual pulses 20 and 22. The first pulse is a measuring beam 20 here. It has an intensity $I_M$ The intensity $I_M$ is not sufficient to evaporate a possible moisture layer 6 on the measuring spot 5 or even to evaporate it partly. In the case shown, the measuring beam 20 has a limited duration. It has a pulse shape. At a second time t1, the laser diode 2 emits the power pulse 22 having the second intensity $I_L$ This intensity and the pulse duration shown symbolically here are chosen such that, in combination, they are sufficient to evaporate the moisture layer 6 which may be located on the measuring spot 5 during the duration of the power pulse 22.

Following the power pulse 22, the laser diode 2 again emits a measuring beam 20, here too again in the form of a pulse having a first intensity $I_M$. The start of this pulse is made immediately after the end of the power pulse 22. However, a small time spacing is entirely possible here but the time period should be chosen such that a moisture layer can be deposited on the surface bf the measuring spot 5 again. This sequence of pulses, containing a measuring beam 20 before a power pulse 22 and a renewed subsequent measuring beam 20, is repeated periodically. With the first measuring beam 20, an electric signal can be generated at the photodiode 8, in this case being a measured signal 28. By the power pulse 22, possible dampening or moisture layers 6 on the surface of the measuring spot 5 are then evaporated, and with the following measuring beam 20, a reference signal 24 is then generated at the photodiode 8.

FIG. 6B shows another possible signal sequence for the photodiode 8. A measuring beam 20 is emitted virtually continuously. This measuring beam 20 is interrupted periodically by the power beam 22, which evaporates moisture on the measuring spot 5 if it should be present. At specific times t2 and t3, in each case measured signals 23 and reference signals 24 can be generated by the photodiode 8 in a manner analogous to that described above.

The power pulse 22 begins at a time t1. Its duration and intensity $I_L$ should also be chosen appropriately here in order to evaporate a possible moisture layer 6 on the measuring spot 5. Following a time t3, the reference signal 24 is then generated at the photodiode 8 by the measuring beam 20.

Figure 7:
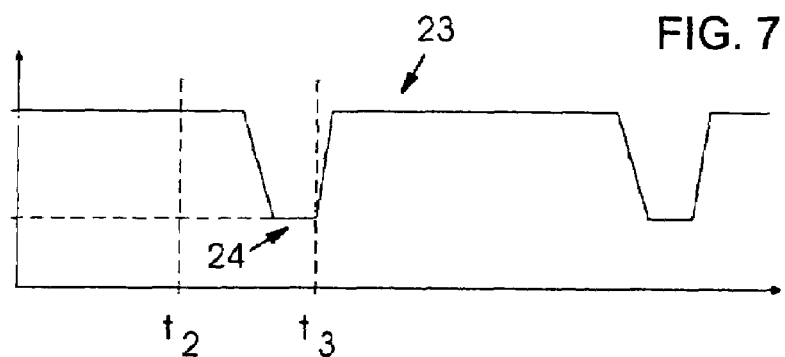
FIG. 7 is a graph showing a representation over time of the measured signal waveform from a photodiode.

FIG. 7 illustrates a possible waveform over time of an electronic signal which is generated at the photodiode 8. The origin of the signal waveform shown here in this case lies in the signal sequence for the photodiode 8 as illustrated in FIG. 6B. At times during which a possible moisture layer 6 on the measuring spot has not been evaporated by a power pulse 22, the measured signal 23 is present. At the times during which no layer is definitely present on the measuring spot 5, a reference signal 24 is generated at the photodiode 8. Should there be no moisture layer 6 on the measuring spot 5 during the entire time period, then both the measured signal 23 and the reference signal 24 are at the same level. At a time t2, which lies before the power pulse 22, the measured signal 23 is transferred to the evaluation device 9. At a time t3, which is chosen such that there is definitely no dampening layer 6 on the measuring spot 5, the reference signal 24 is transferred to the evaluation device 9.

Figure 8:
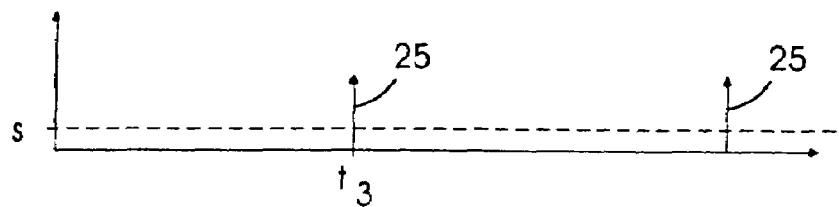
FIG. 8 is a graph showing the representation over time of the difference signals.

FIG. 8 illustrates possible difference signals 25 which are generated by the evaluation device 9 at specific times.

The difference signals 25 are generated periodically. They are formed at the time t3 by a reference signal 24 being subtracted from a measured signal 23 which is recorded at the time t2. If there is a moisture layer 6 on the measuring spot 5 before the power pulse 22, then the difference signal 25 yields a positive value. If there is no moisture layer 6 on the measuring spot 5 before the power pulse 22 either, then the difference signal 25 will be substantially zero. If the magnitude of the difference signal 25 is greater than a specific threshold value s, then a moisture layer on the measuring spot 5 is detected. It is then possible for suitable measures to be taken in order to prevent damage to the plate exposer. Suitable measures can include, for example, switching off the printing plate exposer or special drying of the room in which the plate exposer is located.

Combinations of the apparatus presented here are also conceivable. In particular, provision can also be made for a second laser diode 2' (shown by dashed lines in FIG. 1) to be used for the emission of the power pulse 22. In this case, provision can in particular be made for the wavelength of the emitted power, pulse 22 and the surface composition, for example the material of the measuring spot 5, to be matched to each other in such a way that evaporation of a moisture layer 6 is assisted better. Here, provision can in particular be made for the measuring spot 5 to absorb light in particular of the wavelength of the power pulse 22 particularly well and to be particularly conductive.

This application claims the priority, under 35 U.S.C. § 119, of German patent application No. 10 2004 061 189.0, filed Dec. 20, 2004; the entire disclosure of the prior application is herewith incorporated by reference.

I claim:

1. An apparatus for detecting a moisture on a measuring spot in an exposer for printing forms, the apparatus comprising:
    a radiation source configured for emitting radiation;
    at least one level controller configured for driving at least said radiation source at least for an emission of a measuring beam having a first intensity to generate a measuring signal determined from the radiation reflected from the measuring spot and a power pulse having a second intensity, being higher than the first intensity, for a substantially complete evaporation of the moisture on the measuring spot;
    a photoelectric converter configured for detecting the radiation reflected or scattered by the measuring spot, the radiation being emitted by said radiation source having a wavelength lying within an absorption wavelength range of the moisture on the measuring spot; and
    an evaluation device configured for comparing the measuring signal dependent on the radiation reflected from the measuring spot with an electric reference signal determined from radiation reflected from a dry measuring spot.

2. The apparatus according to claim 1, further comprising a further radiation source driven by said level controller, said further radiation source being configured for emitting the power pulse.

3. The apparatus according to claim 2, wherein said further radiation source emitting radiation having a wavelength within the absorption wavelength range of a surface of the measuring spot.

4. The apparatus according to claim 3, wherein the surface of the measuring spot contains at least one absorber layer for a wavelength range which includes the wavelength of at least one of said radiation source and said further radiation source.

5. The apparatus according to claim 3, wherein the surface of the measuring spot is a thermally conductive layer.

6. The apparatus according to claim 1, further comprising at least one active cooling element for cooling the measuring spot.

7. A method for detecting moisture on a measuring spot in an exposer for printing forms, which comprises the steps of:
   providing an apparatus having an evaluation device, a radiation source and a photoelectric converter for detecting radiation reflected or scattered by the measuring spot;
   emitting radiation from the radiation source having a wavelength lying within an absorption wavelength range of the moisture on the measuring spot by emitting at least one measuring beam having a first intensity from the radiation source;
   generating a measured signal at the photoelectric converter;
   evaporating the moisture on a surface of the measuring spot;
   generating an electric reference signal as a result of reflection of another measuring beam having the first intensity at the surface of a dry measuring spot following the evaporating step for evaporating the moisture; and
   comparing, in the evaluation device, the measured signal from the radiation reflected from the measuring spot with the electric reference signal from the radiation reflected from the dry measuring spot.

8. The method according to claim 7, which further comprises emitting a power pulse having a second intensity which is higher than the first intensity for evaporating the moisture.

9. The method according to claim 8, which further comprises emitting the power pulse using a further radiation source.

10. The method according to claim 9, which further comprises setting a wavelength range for radiation emitted from the further radiation source to lie within a wavelength range in which the surface of the measuring spot absorbs radiation.

11. The method according to claim 7, which further comprises forming a difference signal from the measured signal and the electric reference signal.

12. The method according to claim 11, wherein beginning at a threshold value of the difference signal, detecting condensed moisture on the measuring spot.

13. The method according to claim 7, which further comprises generating the measured signal and the electric reference signal in dependence on an intensity of reflected radiation.

14. The method according to claim 7, which further comprises generating the measured signal and the electric reference signal in dependence on an intensity of scattered light from a radiation incident on the measuring spot.

15. The method according to claim 7, which further comprises generating the measured signal and the electric reference signal in dependence on a plane of polarization of the radiation reflected from the measuring spot.

16. The method according to claim 7, which further comprises generating the measured signal and the reference signal in dependence on a reflection angle of the radiation reflected from the measuring spot.

17. The method according to claim 7, which further comprises actively cooling the measuring spot.

18. The method according to claim 8, which further comprises varying an amount of energy of the power pulse in successive measurements.

19. The method according to claim 18, which further comprises varying the amount of energy such that, starting from a minimum value, the energy is increased until no changes in successive reference signals are detected.

20. The method according to claim 18, which further comprises varying the amount of energy by changing the second intensity of the power pulse.

21. The method according to claim 18, which further comprises varying the amount of energy by changing a pulse length of the power pulse.

22. A method for detecting a quantity of moisture on a measuring spot in an exposer for printing forms, which comprises the steps of:
   providing an apparatus according to claim 1 for detecting radiation reflected or scattered by the measuring spot;
   emitting radiation from the radiation source having a wavelength lying within an absorption wavelength range of the quantity of moisture on the measuring spot by emitting at least one power pulse having a given intensity from the radiation source;
   monitoring the radiation reflected with the photoelectric converter resulting in reference signals;
   evaluating the reference signals to determine when no changes occur between successive reference signals; and
   determining an amount of energy of the power pulse needed in order that no change occurs in the successive reference signals.

23. The method according to claim 22, which further comprises using the amount of energy of the power pulse needed to determine a thickness of the moisture.

* * * * *